United States Patent
Penias

(10) Patent No.: US 12,004,859 B2
(45) Date of Patent: Jun. 11, 2024

(54) CONTACTLESS AUTOMATED AND REMOTE POLYGRAPH TEST

(71) Applicant: VALID.IT EVALUATION SOLUTIONS LTD, Ramat Hashofet (IL)

(72) Inventor: Yossi Penias, Ramat Hashofet (IL)

(73) Assignee: VALID.IT EVALUATION SOLUTIONS LTD, Ramat Hashofet (IL)

(*) Notice: Subject to any disclaimer, the term of this patent is extended or adjusted under 35 U.S.C. 154(b) by 0 days.

(21) Appl. No.: 18/375,520

(22) Filed: Oct. 1, 2023

(65) Prior Publication Data

US 2024/0032832 A1  Feb. 1, 2024

Related U.S. Application Data

(63) Continuation of application No. PCT/IL2023/050489, filed on May 11, 2023.

(Continued)

(51) Int. Cl.
*A61B 5/16* (2006.01)
*A61B 5/00* (2006.01)
(Continued)

(52) U.S. Cl.
CPC ............ *A61B 5/164* (2013.01); *A61B 5/0022* (2013.01); *A61B 5/004* (2013.01); *A61B 5/0205* (2013.01);
(Continued)

(58) Field of Classification Search
CPC ..... A61B 5/164; A61B 5/0205; A61B 5/7267; A61B 5/7264; A61B 5/021; A61B 5/02405; A61B 5/4266; G06V 40/176
See application file for complete search history.

(56) References Cited

U.S. PATENT DOCUMENTS

| 4,331,160 A * | 5/1982 | Zito, Sr. ............... | A61B 5/0531 600/547 |
| 2007/0270659 A1* | 11/2007 | Giegerich ............ | A61B 5/0002 600/300 |

(Continued)

FOREIGN PATENT DOCUMENTS

WO  WO 2018/151628  8/2018

OTHER PUBLICATIONS

Avital, R., et al. "Machine Learning Methods" (2021); downloaded from the internet Sep. 10, 2023; <<https://fixelalgorithms.gitlab.jo/>>.

(Continued)

*Primary Examiner* — Manuel L Barbee
(74) *Attorney, Agent, or Firm* — PEARL COHEN ZEDEK LATZER BARATZ LLP

(57) ABSTRACT

A computer-implemented method for conducting a polygraph test, the method comprising: monitoring physiological indices of a user during the steps of: providing the user with a plurality of pre-questions; and receiving answers from the user to the plurality of pre-questions; analyzing the answers to the pre-questions and physiological indices using machine learning and setting baselines for the monitored physiological indices; generating a plurality of test questions for the user based on the analysis; monitoring physiological indices of a user during the steps of: providing the user with the plurality of test questions; and receiving answers from the user to the test questions; comparing the baselines and the monitored physiological indices during the provision of answers to the test questions; and generating a test result to the test question.

20 Claims, 9 Drawing Sheets

Related U.S. Application Data

(60) Provisional application No. 63/340,939, filed on May 12, 2022.

(51) Int. Cl.

| | | |
|---|---|---|
| *A61B 5/0205* | (2006.01) | |
| *A61B 5/021* | (2006.01) | |
| *A61B 5/024* | (2006.01) | |
| *A61B 5/08* | (2006.01) | |
| *A61B 5/11* | (2006.01) | |
| *A61B 5/117* | (2016.01) | |
| *G06V 40/16* | (2022.01) | |

(52) U.S. Cl.
CPC ............ *A61B 5/117* (2013.01); *A61B 5/7267* (2013.01); *G06V 40/176* (2022.01); *A61B 5/021* (2013.01); *A61B 5/02405* (2013.01); *A61B 5/0816* (2013.01); *A61B 5/1107* (2013.01); *A61B 5/165* (2013.01); *A61B 5/4266* (2013.01); *A61B 2560/02* (2013.01); *A61B 2560/0443* (2013.01)

(56) References Cited

U.S. PATENT DOCUMENTS

| | | | | |
|---|---|---|---|---|
| 2011/0040191 | A1* | 2/2011 | Kyle | A61B 5/164 |
| | | | | 348/E5.09 |
| 2014/0370481 | A1* | 12/2014 | Ruiz | G09B 7/02 |
| | | | | 434/327 |
| 2017/0290539 | A1* | 10/2017 | Yaffe-Ermoza | A61B 5/0533 |
| 2022/0087584 | A1* | 3/2022 | Kircher | A61B 5/7289 |
| 2022/0354401 | A1* | 11/2022 | Burgoon | G06F 3/041 |
| 2023/0052100 | A1* | 2/2023 | Devani | A61B 5/4088 |
| 2023/0109763 | A1* | 4/2023 | Everman | A61B 5/02416 |
| | | | | 600/408 |
| 2023/0153407 | A1* | 5/2023 | Van Rest | G06F 21/32 |
| | | | | 713/186 |

OTHER PUBLICATIONS

Burges.; "From RankNet to LambdaRank to LambdaMART: An Overview"; published 2010; Microsoft Research Technical Report MSR-TR-2010-82.

Li.: "A Short Introduction to Learning to Rank "; published 2011; J-Stage; IEICE Transactions on Information and Systems vol. E94.D Issue 10 pp. 1854-1862.

Pang et al.; "SetRank: Learning a Permutation-Invariant Ranking Model for Information Retrieval"; published Jul. 25, 2020; SIGIR '20: Proceedings of the 43rd International ACM SIGIR Conference on Research and Development in Information; pp. 499-508.

XGBoost; extreme Gradient Boosting; released May 9, 2022; https://github.com/dmmic/xoboost.

LightGBM; Light Gradient Boosting Machine; released Jan. 7, 2022; https://github.com/microsoft/LightGBM).

Catboost; Yandex CatBoost; released Apr. 7, 2022; http://github.com/catboost/catboost.

Babajee et al.; "Identifying Human Emotions from Facial Expressions with Deep Learning":published Aug. 7, 2020; Zooming Innovation in Consumer Technologies.

Pisankski et al.; "Human Stress Detection: Cortisol Levels in Stressed Speakers Predict Voice-Based Judgments of Stress"; published Dec. 10, 2020; Sage Publications; vol. 50, Issue 1.

Mememoji; Facial Emotion Recognition; released Dec. 20, 2016;https://github.com/JostineHo/mememoji.

* cited by examiner

100

```
┌─────────────────────────────────────────────────┐
│ MONITORING PHYSIOLOGICAL INDICES OF A USER      │
│ DURING THE STEPS OF:                            │
│ PROVIDING THE USER WITH A PLURALITY OF PRE-     │ 102
│ TEST QUESTIONS; AND                             │
│ RECEIVING ANSWERS FROM THE USER TO THE          │
│ PLURALITY OF PRE-QUESTIONS                      │
└─────────────────────────────────────────────────┘
                        │
┌─────────────────────────────────────────────────┐
│ ANALYZING THE ANSWERS TO THE PRE-               │
│ QUESTIONS AND PHYSIOLOGICAL INDICES USING       │ 104
│ MACHINE LEARNING AND SETTING BASELINES FOR      │
│ THE MONITORED PHYSIOLOGICAL INDICES             │
└─────────────────────────────────────────────────┘
                        │
┌─────────────────────────────────────────────────┐
│ GENERATING A PLURALITY OF TEST QUESTIONS        │ 106
│ FOR THE USER BASED ON THE ANALYSIS              │
└─────────────────────────────────────────────────┘
                        │
┌─────────────────────────────────────────────────┐
│ MONITORING PHYSIOLOGICAL INDICES OF A           │
│ USER DURING THE STEPS OF:                       │
│ PROVIDING THE USER WITH THE PLURALITY OF        │ 108
│ TEST QUESTIONS; AND                             │
│ RECEIVING ANSWERS FROM THE USER TO THE          │
│ TEST QUESTIONS                                  │
└─────────────────────────────────────────────────┘
                        │
┌─────────────────────────────────────────────────┐
│ COMPARING BASELINES AND THE MONITORED           │
│ PHYSIOLOGICAL INDICES DURING THE PROVISION      │ 110
│ OF ANSWERS TO THE TEST QUESTIONS                │
└─────────────────────────────────────────────────┘
                        │
┌─────────────────────────────────────────────────┐
│ GENERATING A TEST RESULT TO THE TEST            │ 112
│ QUESTIONS                                       │
└─────────────────────────────────────────────────┘
```

FIG. 1

| Question No. | ID | Language ID | Dynamic values | Regular appropriate | Language | Type | Answer | Content |
|---|---|---|---|---|---|---|---|---|
| 1 | 1 | 1.0 | [["name", "FULL_YEAR", "rule_id: 3]] | Yes | English | IR | True | Is this the year 2022? |
| 2 | 4 | 1.0 | | Yes | English | SCR | True | Do you intend to answer all questions by telling the truth? |
| 3 | 279 | 1.0 | | No | English | C | True | Is there a change you have ever behaved irresponsibly? |
| 4 | 358 | NaN | NaN | Yes | English | R | True | Is the information that appears in the claim....? |
| 5 | 264 | 1.0 | | No | English | C | True | Have you ever done something that could lead |
| 6 | 5 | 1.0 | [["name", "FULL_NAME", "rule_id: 2]] | Yes | English | SYM | True | Is your name X Y? |

FIG. 6

| HR | SPO2 | RR | SDNN | SL | BP | RRL | Reading time | Question Type |
|---|---|---|---|---|---|---|---|---|
| 66 | 99 | 16 | 0 | 0 | 0 | 0 | 15:24:25 | C |
| 66 | 99 | 16 | 0 | 0 | 0 | 0 | 15:24:26 | |
| 66 | 99 | 17 | 0 | 0 | 0 | 0 | 15:24:27 | |
| 66 | 99 | 17 | 0 | 0 | 0 | 0 | 15:24:28 | |
| 66 | 99 | 17 | 0 | 0 | 0 | 0 | 15:24:29 | |
| 63 | 99 | 17 | 0 | 0 | 0 | 0 | 15:24:30 | |
| 63 | 99 | 18 | 0 | 0 | 0 | 0 | 15:24:31 | |
| 63 | 99 | 18 | 0 | 0 | 0 | 0 | 15:24:32 | Break |
| 63 | 99 | 19 | 0 | 0 | 0 | 0 | 15:24:33 | |
| 63 | 99 | 20 | 0 | 0 | 0 | 0 | 15:24:34 | |
| 75 | 99 | 20 | 0 | 0 | 0 | 0 | 15:24:35 | |
| 75 | 99 | 21 | 0 | 0 | 0 | 0 | 15:24:36 | |
| 75 | 99 | 21 | 0 | 0 | 0 | 0 | 15:24:37 | |
| 75 | 99 | 21 | 0 | 0 | 0 | 0 | 15:24:38 | |
| 75 | 99 | 21 | 0 | 0 | 0 | 0 | 15:24:39 | R |
| 73 | 99 | 21 | 0 | 0 | 0 | 0 | 15:24:40 | |
| 65 | 99 | 22 | 0 | 0 | 0 | 0 | 15:24:41 | |
| 58 | 99 | 22 | 0 | 0 | 0 | 0 | 15:24:42 | |
| 58 | 99 | 23 | 0 | 0 | 0 | 0 | 15:24:43 | |
| 58 | 99 | 23 | 0 | 0 | 0 | 0 | 15:24:44 | |
| 58 | 99 | 23 | 0 | 0 | 0 | 0 | 15:24:45 | |

FIG. 7

CONTACTLESS AUTOMATED AND REMOTE POLYGRAPH TEST

CROSS-REFERENCE TO RELATED APPLICATIONS

This application is a continuation of PCT International Application No. PCT/IL2023/050489, International Filing Date May 11, 2023, claiming the benefit of U.S. Provisional Application No. 63/340,939, filed May 12, 2022, which are hereby incorporated by reference.

TECHNICAL FIELD OF THE INVENTION

The present invention relates generally to methods of assessing changes to physiological parameters of humans in response to interrogations, and more specifically to the conduction of polygraph tests using machine learning.

BACKGROUND OF THE INVENTION

A polygraph is a device for the recording and analysis of physiological indicators during an interrogation of a testee. Detected changes in physiological behavior of a testee when exposed to questions of a polygraph test and during the provision of answers to the questions are analyzed to identify whether a testee responded to a question by telling a lie or telling the truth.

Polygraph tests have widely been used as an interrogation tool in the examination of criminal suspects by various law enforcement agencies. The tests performed today use a physical measuring instrument and require the physical presence of a human examiner to interview a testee during the conduction of the test.

Present polygraph tests commonly monitor four physiological indicators of a testee during a test: blood pressure, sweating, respiration, and blood saturation.

Generally, a lie/the truth in response to a test question is identified through a comparison of changes to physiological indicators between relevant questions (known as R questions) that are asked, for example, to interrogate a testee about a particular incident for which an indication of a true or false answer to a question is desired and test questions that are routinely asked to provide a benchmark, also referred to as control questions (known as C questions). This type of interrogation method is called CQT.

The interpretation of biological indicators allows an assessment as to whether a testee has answered a question by telling the truth or telling a lie. For example, when a C question results in a stronger physiological response—identified by measurement of the physiological indicators—than a physiological response by a testee to an R question, the answer provided by a testee in response to the R question is considered as answered truthfully and vice versa.

The interpretation of physiological indicators depends mainly on the examiner's subjective interpretation. As a result, human polygraph examiners commonly conduct polygraph tests according to their subjective impression of the testee's the behavior.

For example, during the polygraph test, a human examiner may bias the response of a testee to a test question through their interrogation style (pronunciation, accent, pause between words, stuttering, etc.). Accordingly, not every question that produces a response by a testee to a test question allows an assessment with a high degree of certainty as to whether the testee's answer is true or false. Thus, the outcome of a polygraph test may be biased by the subjective view of an examiner.

Therefore, there is a need to perform a polygraph test remotely and in the absence of a human examiner to reduce the subjective influence of a human examiner in the generation of polygraph test questions and in the assessment of answers provided by a testee in response to the test questions.

SUMMARY OF THE INVENTION

Improvements and advantages may include performing a polygraph test remotely. The fact that there is no human factor involved in the process makes it possible to save costs and to provide a polygraph test atmosphere that is free of biases and external influences in comparison to a test that requires the presence of an examiner.

Improvements and advantages may also include performing a polygraph test using test questions that are dynamically generated via machine learning based on the analysis of answers provided to questions and physiological indices that are monitored during the polygraph test. Thereby, machine learning allows to generate test questions that are adapted to the responsiveness and behavior of a user to previous questions, e.g. pre-questions, of a polygraph test. Machine learning-generated test questions are generated by the system and methods disclosed herein taking into account the responsiveness and behavior of a user to previous questions. The systems and methods disclosed herein may allow the generation of test questions that allow the differentiation of a lie or a truthful answer to a question with a higher precision compared to polygraph tests conducted by human examiners.

Embodiments include performing a remote and contactless polygraph test without the involvement of a human examiner. Embodiments include discriminating lies from truth by measuring physiological indices related to the sympathetic system.

One embodiment may include a computer-implemented method for conducting a polygraph test, the method comprising: monitoring physiological indices of a user during the steps of: providing the user with a plurality of pre-questions; and receiving answers from the user to the plurality of pre-questions; analyzing the answers to the pre-questions and physiological indices using machine learning and setting baselines for the monitored physiological indices; generating a plurality of test questions for the user based on the analysis; monitoring physiological indices of a user during the steps of: providing the user with the plurality of test questions; and receiving answers from the user to the test questions; comparing baselines and the monitored physiological indices during the provision of answers to the test questions; and generating a test result to the test questions.

In one embodiment, monitoring of physiological indices comprises measurement of cardio and respiratory factors.

In one embodiment, the physiological indices are selected from a group consisting of: blood pressure, sweat, heart pulse, breathing parameters such as lung capacity or tidal volume, heart rate variation (HRV), respiratory rate (RR+), voice stress analysis and micro-reactions in the facial muscles. For example, breathing of a user may be analyzed during a polygraph test by monitoring one or more of: lung capacity, respiratory rate, the tidal volume, minute ventilation, time between inhaling and exhaling of air.

In one embodiment, baselines are continuously recalculated during the test questions based on dynamic monitoring of the physiological indices.

In one embodiment, baselines are adjusted to the behavior of the user during the pre-questions and the test questions.

In one embodiment, the plurality of pre-questions comprises questions on one or more of: personal data, credibility, personality traits and stimulation of the user.

In one embodiment, the physiological indices are monitored using video processing of the user's face.

In one embodiment, the monitored physiological indices are analyzed using machine learning to identify deviations in the physiological indices compared to the baseline value for a physiological index.

In one embodiment, the content of the plurality of test questions is dynamically adjusted using machine learning based on the received answers to the pre-questions.

In one embodiment, the dynamical adjustment of the content of the plurality of test questions enables the generation of questions with an increased discernment in the monitored physiological indices upon answering the questions.

In one embodiment, the sequence of the plurality of test questions is dynamically adjusted based on the received answers to the pre-questions.

In one embodiment, the plurality of test questions comprises a question to identify the user.

In one embodiment, the polygraph test is conducted remotely in the absence of a human examiner.

In one embodiment, comparison of baselines and the monitored physiological indices during the provision of the testee's answers to the test questions allows identification of the physiological indices with the largest percentage deviation relative to baselines in the generation of test results for the test questions.

An embodiment may include a system for conducting a polygraph test, the system may include: a computing device; a memory; and a processor, the processor configured to: monitor physiological indices of a user during the steps of: providing the user with a plurality of pre-questions and receiving answers from the user to the plurality of pre-questions; analyze the answers to the pre-questions and physiological indices using machine learning; set baselines for the monitored physiological indices; generate a plurality of test questions for the user based on the analysis; monitor physiological indices of a user during the steps of: providing the user with the plurality of test questions; and receiving answers from the user to the test questions; compare baselines and the monitored physiological indices during the provision of answers to the test questions; and provide a test result to the test questions.

In one embodiment, the monitoring of physiological indices comprises measurement of cardio and respiratory factors.

In one embodiment, the physiological indices are selected from a group consisting of: blood pressure, sweat, heart pulse, breathing, heart rate variation, respiratory rate, voice stress analysis and micro-reactions in the facial muscles.

In one embodiment, the baselines are continuously recalculated during the test questions based on dynamic monitoring of the physiological indices.

In one embodiment, the baselines are adjusted to the behavior of the user during the pre-questions and the test questions.

An embodiment may include a computer-implemented method for carrying out a polygraph test, the method comprising: measuring physiological parameters of a user during the steps of: sending to the user a first series of test questions; and collecting answers from the user to the first series of questions; analyzing the answers to the first series of test questions and physiological parameters using machine learning; calculating baselines for the monitored physiological parameters; generating a second series of test questions for the user based on the analysis; measuring physiological parameters of a user during the steps of: sending to the user the second series of test questions; and receiving answers from the user to the second series of test questions; comparing the baselines and the monitored physiological parameters during the provision of answers to the second series of test questions; and providing a test result to the second series of test questions. These, additional, and/or other aspects and/or advantages of the present invention may be set forth in the detailed description which follows; possibly inferable from the detailed description; and/or learnable by practice of the present invention.

BRIEF DESCRIPTION OF THE DRAWINGS

The subject matter that is regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 1 is a flowchart of a computer-implemented method for conducting a polygraph test, according to embodiments of the present invention;

FIG. 6 is an exemplary chart showing generated test questions for a polygraph test, according to embodiments of the present invention;

FIG. 7 shows a chart of physiological indices that are recorded during a polygraph test, according to embodiments of the present invention;

Figure 2:
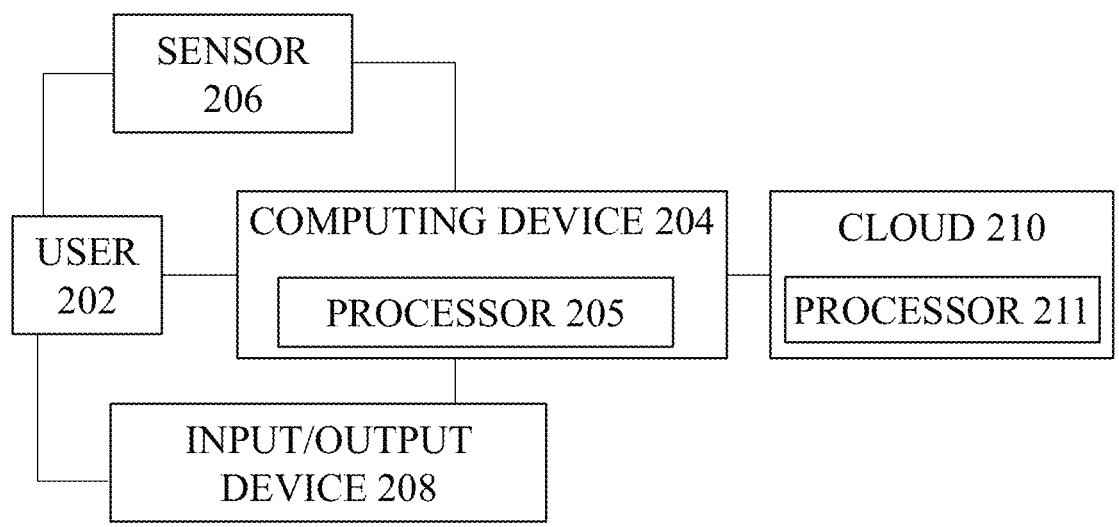
FIG. 2 is a high-level block diagram of the main components of an exemplary system that is required, e.g., for a computer-implemented method for conducting a polygraph test, according to embodiments of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF EMBODIMENTS OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein is for the purpose of description and should not be regarded as limiting.

Unless specifically stated otherwise, as apparent from the following discussions, it is appreciated that throughout the specification discussions utilizing terms such as "processing", "computing", "calculating", "determining", "enhancing" or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices. Any of the disclosed modules or units may be at least partially implemented by a computer processor.

FIG. 1 shows a block diagram of a computer-implemented method 100 for conducting a polygraph test. The example processes shown in FIG. 1 may be carried out by computer system 200, or the system shown in FIG. 2, or another computer system. A user, e.g. user 202 may undergo a polygraph test using a computing device, e.g. computing device 204. Computing device 204 may be a portable computing device, for example a smart phone, tablet or a laptop. Computing device 204 may execute a polygraph test via processor 205. Computing device 204 may be connected to one or more sensors 206. In one embodiment, a sensor, e.g. sensor 206 detects physiological indices of the sympathetic system of a user. In one embodiment, a sensor is, for example, a sensor that detects heart rate, blood pressure or heart rate variability (HRV) of a user. In one embodiment, a sensor is a breath sensor that measures breathing rhythm and/or the respiratory rate (RR). In one embodiment, a sensor is a sensor that measures the sweat of a user. The occurrence of sweat of a user undergoing a polygraph test may be assessed, for example, by measuring the Galvanic Skin Response (GSR) commonly known as the Skin Conductance Level. A variation in conductivity may indicate the occurrence of sweat as a result of a user experiencing stress when confronted with a question during the polygraph test. The occurrence of sweat may also be the result of stress experienced by a user when answering a question of the polygraph test, e.g. during the pre-test or test, by telling a lie. The magnitude in the change of conductivity may correlate to the level of stress experienced by a user. For example, a low change of conductivity may indicate a low level of sweat and, thus, a low level of stress experienced by the user. On the other hand, a high change of conductivity may indicate a high level of sweat and, thus, a high level of stress experienced by the user. A sensor, e.g. sensor 206, may measure physiological indices of a user e.g. user 202.

Physiological indices of a user, such as user 202, may also be measured using computing device 204. Computing device 204 may be connected to an input and/or output device, e.g. input/output device 208. Input/output device 208, may be, for example, a photo camera, a video camera or a microphone. In one embodiment, device 208 may be integrated into computing device 204.

Input/output device 208 may allow audio recording of a user, e.g. user 202 during the polygraph test. In one embodiment, a sensor is a touch screen of a computing device, e.g. of a smart phone, tablet or laptop. In one embodiment, a sensor may be any available sensor of a computing device, for example screen click power or cell phone tilt.

Device 208 may be used for the recording of voice, for example the user's voice, during the polygraph test. For example, voice recordings during the polygraph test may allow the recording of an answer of a user to a test question. Additionally, voice recordings may be used to conduct a voice-stress analysis. Device 208 may also be used to record images or video sequences of a user during a polygraph test. Images or video recordings of a user, e.g. user 202, may be generated during a polygraph test and the recordings may be used, for example, to identify micro-reactions in the facial muscles. Device 208 may also be an output device, for example, a loud speaker. A loud speaker may provide a user with test questions. Device 208 may be, for example, a monitor, e.g. laptop monitor or smart phone display, to provide a user with test question via visual display. Recorded physiological indices, audio recordings, image recordings or videos recordings may be stored in memory of computing device 204.

In an embodiment, computing device 204 may be connected to a computing device, for example cloud 210. Cloud 210 may include processor 211. Cloud 210 may be configured to store and process recorded physiological indices, audio recordings, image recordings or videos recordings of a user, e.g. user 202 conducting a polygraph test.

A system as disclosed herein may include a computing device 204, such as computing device 300; a memory; and a processor 205. A processor may be configured to receive physiological indices of a user. Alternatively, a processor may be configured to receive recorded physiological indices, audio recordings, image recordings or videos recordings of a user. A processor may be configured to calculate dimensionless physiological indices of a user based on received physiological indices of a user.

Figure 3:
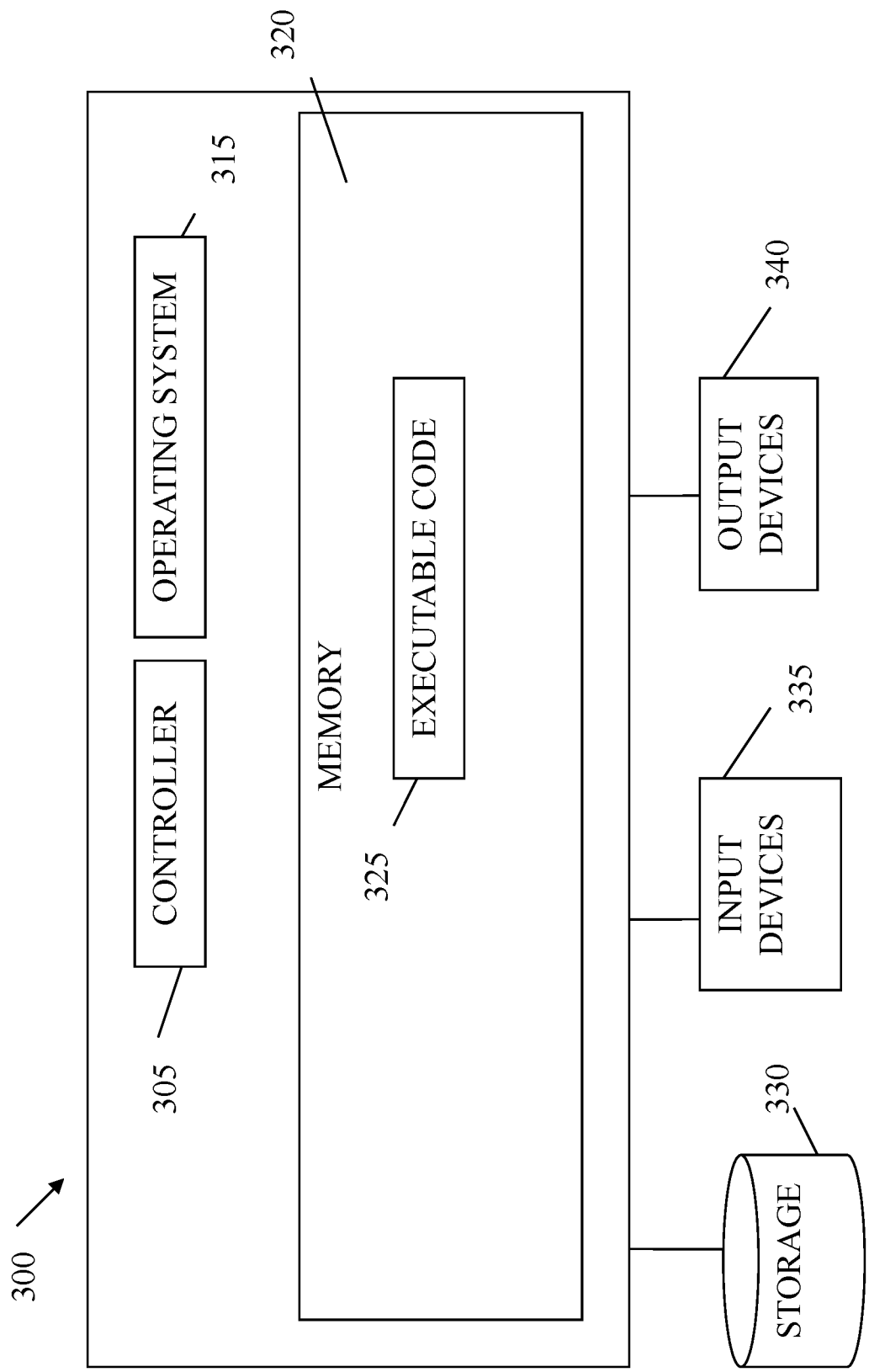
FIG. 3 is a high-level block diagram of an exemplary system, according to embodiments of the present invention.

Computing device 300 may include a controller or processor 305 that may be, for example, a central processing unit processor (CPU), a chip or any suitable computing or computational device, an operating system 315, a memory 320, a storage 330, input devices 335 and output devices 340 such as a computer display or monitor displaying for example a computer desktop system. Each of modules and equipment and other devices and modules discussed herein, e.g. a computing device 204, cloud 210, or the computer systems and modules in FIG. 2, etc. may be or include, or may be executed by, a computing device such as included in FIG. 3 although various units among these modules may be combined into one computing device.

Operating system 315 may be or may include any code segment designed and/or configured to perform tasks involving coordination, scheduling, arbitration, supervising, controlling or otherwise managing operation of computing device 300, for example, scheduling execution of programs. Memory 320 may be or may include, for example, a Random Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 320 may be or may include a plurality of, possibly different memory units. Memory 320 may store for example, instructions (e.g. code 325) to carry out a method as disclosed herein, and/or data.

Executable code 325 may be any executable code, e.g., an application, a program, a process, task or script. Executable code 325 may be executed by controller 305 possibly under control of operating system 315. For example, executable code 325 may be one or more applications performing methods as disclosed herein, for example those of FIGS. 2-3 according to embodiments of the present invention. In some embodiments, more than one computing device 300 or components of device 300 may be used for multiple functions described herein. For the various modules and functions described herein, one or more computing devices 300 or components of computing device 300 may be used. Devices that include components similar or different to those included in computing device 300 may be used, and may be connected to a network and used as a system. One or more processor(s) 305 may be configured to carry out embodiments of the present invention by, for example, executing software or code. Storage 330 may be or may include, for example, a hard disk drive, a floppy disk drive, a Compact Disk (CD) drive, a CD-Recordable (CD-R) drive, a universal serial bus (USB) device or other suitable removable and/or fixed storage unit. Data may be stored in a storage 330 and may be loaded from storage 330 into a memory 320 where it may be processed by controller 305. In some embodiments, some of the components shown in FIG. 3 may be omitted.

Input devices 335 may be or may include a mouse, a keyboard, a touch screen or pad or any suitable input device. It will be recognized that any suitable number of input devices may be operatively connected to computing device 300 as shown by block 335. Output devices 340 may include one or more displays, speakers and/or any other suitable output devices. It will be recognized that any suitable number of output devices may be operatively connected to computing device 300 as shown by block 340. Any applicable input/output (I/O) devices may be connected to computing device 300, for example, a wired or wireless network interface card (NIC), a modem, printer or facsimile machine, a universal serial bus (USB) device or external hard drive may be included in input devices 335 and/or output devices 340.

Embodiments of the invention may include one or more article(s) (e.g. memory 320 or storage 330) such as a computer or processor non-transitory readable medium, or a computer or processor non-transitory storage medium, such as for example a memory, a disk drive, or a USB flash memory, encoding, including or storing instructions, e.g., computer-executable instructions, which, when executed by a processor or controller, carry out methods disclosed herein.

Some embodiments may include monitoring physiological indices of a user during the steps of: providing the user with a plurality of pre-questions; and receiving answers from the user to the plurality of pre-questions (step 102). In an embodiment, a processor e.g. processor 204 of computing device 205 is configured to monitor physiological indices of a user during the steps of: providing the user with a plurality of pre-test questions; and receiving answers from the user to the plurality of pre-questions.

In one embodiment, monitoring physiological indices of a user includes obtaining measured physiological data from a user, e.g. user 202. For example, physiological indices for a user are periodically received during the polygraph test at a computing device, e.g. computing device 204.

Physiological indices may be received via a computing device, e.g. computing device 204, or via a sensor, e.g. sensor 206. A sensor may be configured to record audio or video recordings of user 202. For example, sensor 206 may be configured to record voice recording or micro-reactions in facial muscles, for example eye movement. Additionally, a sensor may be configured to record physiological indices of user 202, for example a sensor is a bio indicator extractor (BINAH).

Physiological indices may comprise physiological indices such as blood pressure, sweat, heart rate, breathing, heart rate variation, respiratory rate. In one embodiment, computing device 204 is configured to provide user 202 with audio recordings. For example, computing device 204 may be configured to release audio messages to user 202 such as pre-questions, test questions and/or test instructions.

Physiological indices may be measured using a photo or video recording device, e.g. photo or video recording device 208. Device 208 may record videos or images of the user's face. Images may be recorded periodically, e.g. every 1/30 second). Alternatively, images may be extracted from recorded videos. Comparison of image sequences during the test may allow to identify changes to the skin muscles of a user. For example, using a volume sensor, changes to the appearance of the user's skin may be affected by the concentration of blood present in tissues making up the skin such as Epidermis, Dermis and Hypodermis.

In one embodiment sensor 206 is an audio sensor and is configured to record voice recordings of user 202, for example sensor 206 is configured to record an answer given by user 202 to a question transmitted to user 202. For example, voice recordings of a user may be analyzed as known in the art: Cortisol levels for a user may be calculated as disclosed by Pisanski and Sorokowski (Human Stress Detection: Cortisol Levels in Stressed Speakers Predict Voice-Based Judgments of Stress, Perception, Volume 50, issue 1, pages 80-87, https://doi.org/10.1177/0301006620978378), herein incorporated by reference. In one embodiment, a processor e.g. processor 204 of computing device 205 is configured to monitor physiological indices of a user during the steps of: providing the user with a plurality of pre-questions; and receiving answers from the user to the plurality of pre-questions.

In one embodiment, physiological indices, for example voice recordings of user 202 are measured at the beginning of the polygraph test and a baseline of the voice recording may be generated. For example, physiological indices may be measured for 10-20 seconds at the beginning of the polygraph test. The generated baselines of physiological indices, e.g. voice recording may be periodically compared with physiological indices, e.g. voice recordings of the user during the polygraph test. For example, a voice recording measured at the beginning of the polygraph test may be compared with a voice recording obtained when user 202 responded to a question, e.g. a test question.

Physiological indices recorded via computing device 204, sensor 206 and/or input/output device 208 may be recorded in various data formats. To enable a comparison of different physiological indices, data received for each of the physiological indices is normalized to dimensionless physiological indices. A value xi for a physiological index, e.g. heart rate, may be normalized to normalized value zi using Formula 1:

$$z_i = (x_i - \min(x))/(\max(x) - \min(x)) \cdot 100 \quad \text{Formula 1}$$

For each physiological index, minimum value min(x) and maximum value max(x) may be recorded for a specific time period, for example during a polygraph test or in a time window in which physiological indices of a user's answer to a pre-test or test question are monitored. For example, during the pre-test of a polygraph test, a minimum heart rate min(x)heart_rate of a user is recorded as 70 beats per minute (bpm) and a maximum heart rate max(x)heart_rate of a user is recorded as 90 bpm. Subsequent measured values $x_i$ for a physiological index, e.g. heart rate, may be calculated by subtracting the minimum value min(x) from measured value $x_i$ and dividing the value by the difference of maximum value max(x) and minimum value min(x) multiplied by 100.

For example, a min(x)heart_rate=70 bpm, a max(x)heart=90 bpm and a measured value $x_i$_heart_rate=75 bpm would lead to a normalized physiological index $z_i$=25. The normalization using Formula 1 may allow to compare variations in physiological indices that are measured in mixed units, for example bpm (heart rate) and S·m [kg−1·m−3·s3·A2] (electrical conductivity).

The system as disclosed herein may allow dynamic adjustment of a baseline for a physiological index by monitoring minimum and maximum values as well as an average value for a physiological index during the polygraph test and may amend normalized values generated for a physiological index during the polygraph test based on the monitored values. Thereby, a change in a physiological index may be evaluated relative to previously generated values for a physiological index to identify physiological changes in user behavior occurring as a result of a specific event in the polygraph test, for example in response to the provision of an answer to a polygraph test question, in relation to changes in physiological indices that naturally occur during the polygraph test. Normalization of the monitored physiological indices may allow to assess changes to a physiological index independently from the physical unit in which they are recorded.

Thereby, changes between two or more different physiological indices become comparable, e.g. changes two or more different physiological indices may be compared using machine learning.

In an embodiment, normalized indices for a plurality of monitored physiological indices may be separately compared to their set baselines during the provision of answers to the test questions.

In one embodiment, the normalization of physiological indices to dimensionless physiological indices is performed using machine learning. For example, a machine learning algorithm used for the normalization may be a Random Forest algorithm or a decision tree algorithm. In one embodiment, the normalization proceeds via an artificial neural network. In one embodiment, the normalization of physiological indices to dimensionless physiological indices is performed using machine learning via machine learning using processor 211 of cloud 210.

Comparison of the relative changes of the dimensionless physiological indices may allow to identify physiological indices that are more sensitive to the behavior of a user undergoing a polygraph test. The increased sensitivity of a specific physiological index may allow a machine learning algorithms to differentiate whether a question has been answered truthfully or by telling a lie with a higher certainty. Thereby, the choice to rely on indices with a higher sensitivity may allow to improve the identification of a true or a false statement given by a user during the test. In one embodiment, physiological indices are monitored for a pre-defined time period after a question has been transmitted to a user, e.g. via the provision of a voice recording or displayed on a display of computing device 202. For example, physiological indices are monitored for a time period of 10 seconds from the point of providing a question to the user. The normalized physiological indices calculated from physiological indices that are obtained at the time of providing the user with a question and 10 seconds after the provision of a user with a question are compared to a mean, normalized value for each physiological index obtained at the start of the polygraph test.

At the beginning of a polygraph test, during a START phase, physiological indices are recorded and the recorded indices are normalized using machine learning to generate dimensionless physiological indices. In an embodiment, at least two physiological indices are monitored for a specific time interval during the START phase. For example, physiological indices for a user may be monitored for a specific time interval, for example 15-20 seconds. In a START phase of the polygraph test, a user is provided with pre-questions. For example, a user may be provided with pre-questions to provide personal data, for example name, identification number, address.

Pre-questions may be provided to a user in a CHARGE phase. In the CHARGE phase, a user may be provided with pre-questions concerning their self-esteem and the degree of their credibility, for example how they assess their own readability when questioned by a polygraph test. In an embodiment, a user may be provided with selected answers to pre-questions in the CHARGE phase. During the CHARGE phase, physiological indices are recorded and the recorded indices are normalized to generate dimensionless physiological indices and are compared to baselines generated in the START phase.

Pre-questions may be provided to a user in a QUALITIES phase. In the QUALITIES phase, a user is provided with questions to select 5 multiple personality traits from a list of 40 traits (20 positives and 20 negatives). The system as disclosed herein may be configured to use the personality traits, for example in the generation of C questions or in the assessment how a user reacts to a deliberate lie to a question. During the QUALITIES phase, physiological indices are monitored and the monitored indices are normalized to generate dimensionless physiological indices and are compared to the baselines of the START phase and the dimensionless physiological indices of the CHARGE phase.

Pre-questions may be provided to a user in a STIMULATION (STIM) phase. In the STIM phase, a user may be asked to deliberately lie in response to pre-questions provided to him. For example, a user may be exposed to a pre-question that is likely to pose a reduced threat to the user. A reduced threat may be a lie concerning the name of the day of a week or a lie in response to the question "In what year we are in?". During the STIM phase, physiological indices are recorded and the recorded indices are normalized to generate dimensionless physiological indices and are compared to the baselines of the START phase, the dimensionless physiological indices of the CHARGE phase and the dimensionless physiological indices of the QUALITIES phase.

Some embodiments may include analyzing the answers to the pre-questions and physiological indices using machine learning and setting baselines for the monitored physiological indices (step 104). In an embodiment, a processor, e.g. processor 204 of computing device 205, is configured to analyze the answers to the pre-questions and physiological indices using machine learning and is configured to set baselines for the monitored physiological indices. In one embodiment, a baseline for a monitored physiological index is set by monitoring each of the physiological indices for a specific time interval, for example for 15-20 seconds, at the beginning of the polygraph test (START phase). The monitored values for a physiological index monitored during a specific time interval at the beginning of the polygraph test may be used to calculate a mean value for a physiological index which forms a baseline for the subsequent analysis of answers to test questions. In one embodiment, a baseline generated at the beginning of a polygraph test may be adjusted via machine learning in response to physiological indices monitored when a user answers pre-test questions. For example, a baseline may be adjusted via machine learning during the CHARGE phase, QUALITIES phase and/or STIM phase.

Analyzing the answers to the pre-questions and physiological indices using machine learning may also comprise transmitting analyzed pre-questions and physiological indices to a cloud, e.g. cloud 210, and storing analyzed pre-questions and physiological indices in memory of a cloud.

As used herein, "machine learning", "machine learning algorithms", "machine learning models", "ML", or similar, may refer to models built by algorithms in response to/based on input sample or training data. ML models may make predictions or decisions without being explicitly programmed to do so. ML models require training/learning based on the input data, which may take various forms. In a supervised ML approach, input sample data may include data which is labeled, for example, in the present application, the input sample data may include a transcript of an interaction and a label indicating whether or not the interaction was satisfactory. In an unsupervised ML approach, the input sample data may not include any labels, for example, in the present application, the input sample data may include interaction transcripts only.

ML models may, for example, include (artificial) neural networks (NN), decision trees, regression analysis, Bayesian networks, Gaussian networks, genetic processes, etc. Additionally or alternatively, ensemble learning methods may be used which may use multiple/modified learning algorithms, for example, to enhance performance. Ensemble methods, may, for example, include "Random forest" methods or "XGBoost" methods.

Neural networks (NN) (or connectionist systems) are computing systems inspired by biological computing systems, but operating using manufactured digital computing technology. NNs are made up of computing units typically called neurons (which are artificial neurons or nodes, as opposed to biological neurons) communicating with each other via connections, links or edges. In common NN implementations, the signal at the link between artificial neurons or nodes can be for example a real number, and the output of each neuron or node can be computed by function of the (typically weighted) sum of its inputs, such as a rectified linear unit (ReLU) function. NN links or edges typically have a weight that adjusts as learning proceeds. The weight increases or decreases the strength of the signal at a connection. Typically, NN neurons or nodes are divided or arranged into layers, where different layers can perform different kinds of transformations on their inputs and can have different patterns of connections with other layers. NN systems can learn to perform tasks by considering example input data, generally without being programmed with any task-specific rules, being presented with the correct output for the data, and self-correcting, or learning.

Various types of NNs exist. For example, a convolutional neural network (CNN) can be a deep, feed-forward network, which includes one or more convolutional layers, fully connected layers, and/or pooling layers. CNNs are particularly useful for visual applications. Other NNs can include for example transformer NNs, useful for speech or natural language applications, and long short-term memory (LSTM) networks.

In practice, a NN, or NN learning, can be simulated by one or more computing nodes or cores, such as generic central processing units (CPUs, e.g., as embodied in personal computers) or graphics processing units (GPUs such as provided by Nvidia Corporation), which can be connected by a data network. A NN can be modelled as an abstract mathematical object and translated physically to CPU or GPU as for example a sequence of matrix operations where entries in the matrix represent neurons (e.g., artificial neurons connected by edges or links) and matrix functions represent functions of the NN.

Typical NNs can require that nodes of one layer depend on the output of a previous layer as their inputs. Current systems typically proceed in a synchronous manner, first typically executing all (or substantially all) of the outputs of a prior layer to feed the outputs as inputs to the next layer.

Each layer can be executed on a set of cores synchronously (or substantially synchronously), which can require a large amount of computational power, on the order of 10s or even 100s of Teraflops, or a large set of cores. On modern GPUs this can be done using 4,000-5,000 cores.

Decision trees may refer to a data structure or algorithm including, or capable of representing, a series of linked nodes. Decision trees may be used for classification of a data instance/object into a certain class by interrogating features of the instance/object. The linked nodes may include a root node, at least one leaf node (or terminal node), and likely one or more internal nodes, wherein the root node may be connected to a plurality of child nodes (internal or leaf), the internal nodes may be connected to one parent node (internal or root) and a plurality of child nodes, and the leaf node may be connected to one parent node. To classify an object/instance with a decision tree, it may be traversed, wherein traversal begins at the root node. Each root node or internal node may interrogate a feature of the object in a way that categorizes the object into one of a plurality of categories (often two categories corresponding to two child nodes). Each of these categories may be associated with one of the plurality of connected child nodes, and when an object is found to be in one of the categories, the traversal of the decision tree may move to the associated child node.

This process may continue until the presently considered node of the traversal is a leaf node. Each leaf node may be associated with a class or classification of the object (e.g., satisfactory or unsatisfactory) and may not further interrogate features of the object. In some embodiments, decision trees may be implemented with object-oriented programming. In some embodiments, a decision tree may be constructed based on existing/past data (e.g., existing interaction and/or score data, which may also be associated with an indication of whether the interaction was satisfactory).

Construction of a decision tree may be configured to maximize/minimize a metric, such as constructing a decision tree so as to maximize an information gain metric. In some embodiments, the features that are most important for categorization may be higher up or closer to the beginning/root of the tree, and features that are less important may be further from the root.

It will be understood that any subsequent reference to "machine learning", "machine learning algorithms", "machine learning models", "ML", or similar, may refer to any/all of the above ML examples, as well as any other ML models and methods as may be considered appropriate.

Some embodiments may include generating a plurality of test questions for a user based on the analysis (step 106). In an embodiment, a processor e.g. processor 204 of computing device 205 is configured to generate a plurality of test questions for the user based on the analysis. In an embodiment, test questions may be generated using machine learning, for example a Forest tree algorithm or a neural network algorithm. In an embodiment, a plurality of test questions may include C questions. C questions may be questions that prompt a user to answer the test question with a lie or evoke a scenario in which a user has previously lied in response to a question. In an embodiment, a plurality of test questions may include R questions. R questions may concern subject-matter as to why the user is interrogated in the polygraph test. R questions may be questions for which a differentiation between a true and a false answer is desired. For example, an R question may be a question for a user whether he was present at a crime scene when a crime happened. In an embodiment, a plurality of test questions may include Irrelevant (IR) questions.

IR questions may be questions that are not relevant for the assessment of the user via the polygraph test, for example does the room have a door. For example, an IR question may be a question to a user to reduce the stress that a user is experiencing during the polygraph test. In an embodiment, a plurality of test questions may include Sacrifice (SCR) questions. SCR questions may be questions to which an answer is known in advance. For example, a user may be asked an SCR question may be ask question to a user to reduce the stress that the subject usually experiencing after a change in the physiological indices, for example after telling a lie. In an embodiment, a plurality of test questions may include SYM questions. A user may be asked a SYM question to identify whether a user experiences an underlying issue that is not related to the polygraph test that might affect the outcome of the present polygraph test, for example an unusual or significant event that can divert the subject's attention from the test and produce an incorrect result.

In an embodiment, C questions may be generated using machine learning (CQ GENERATOR), for example a random forest algorithm. For example, C questions may be generated based on the provided answers by a user in phases 1-4. Using machine learning, for example a random Forest algorithm, changes in a baseline monitored in phases 1-4 in response to the content of the questions provided to a user and user's responses to the questions are evaluated. The C test questions may be designed to allow an increased distinction between a true answer and a false answer.

In an embodiment, generated C questions may further be evaluated based on the achieved change in physiological indices for a user. For example, if a C question does not lead to a response that shows a change in any of the physiological indicators that are monitored during the response or only a change within 5% in relation to a baseline, the C question may be classed as unsuccessful in achieving a significant change in physiological indices for a user by the system. In one embodiment, C questions that did not lead to a change in physiological indices are not used for the generation of a test result. However, a C question that show a significant change in physiological indices for a user when responding to the C question may be considered as suitable in its use for the generation of a test result.

In one embodiment, R questions may be generated using machine learning (RQ GENERATOR), such as a random forest algorithm or a decision tree algorithm. For example, R questions may be generated based on the provided answers by a user in phases 1-4. Using machine learning, e.g. a random forest algorithm, questions may be generated that are adapted to the user's answers to the questions of the pre-questions or test questions, for example C questions. For example, using machine learning, questions may create R questions that consider subject-matter previously mentioned by a user in previous question, for example relating to time, act, subject or purpose.

The adaptation of the test questions to the users behavior since the beginning of the test by evaluating the changes to a user's physiological indices may allow the generation of test questions that allow a high degree of distinction in the analysis of the test result, e.g. whether the answer may be considered a lie or the answer being true. For example, a generated R question "Have you stolen money in the past?" is not directed to a specific incident. However, a generated R question "Have you stolen 50$ from Jo's office in Tel Aviv in the last two weeks?" may be linked to a specific event that a user would consider when providing an answer to the question. Thus, adapting test questions to a specific event that is dynamically identified during the polygraph test using machine learning may create a physiological response in a user answering the question that allows a high differentiation of a true answer or lie by assessing the monitored physiological indices during the response.

In one embodiment, the type of test questions and the order of test questions for a user may be determined using machine learning (SEQUENCE GENERATOR), for example via a random forest algorithm. Additionally, machine learning may determine whether a test question should be repeated and if so how many times a test question should be asked before asking the user the next test question. For example, machine learning may evaluate answers from a user to the plurality of pre-questions and physiological indices measured during the pre-test to define an order of the test questions of the polygraph test.

A common order used in polygraph tests is a set of 7 test questions of the types SYM question, IR question, C question R question, C question, IR question and R question. The system disclosed herein may allow to identify the change of physiological indices for a user when answering a test question, for example the first C question. In case that the first C question led to a significant change in physiological indices, an additional IR question may be introduced before the next R question to allow a user's physiological indices to settle before the user is confronted with an R question leading to an amended test question sequence of: SYM question, IR question, C question, IR question, R question, C question, IR question and R question. The settlement of the physiological indices prior to the R question may allow to avoid that the reaction of a user to the previous C question would affect the physiological indices when he is provided with the subsequent R question. In a second example, in case a user provided an answer to an R question and the recorded physiological indices did not allow the generation of a test result that allowed a clear differentiation between lie and truth using machine learning, the sequence of the test questions may be adapted to repeat the question at a later stage of the polygraph test.

In a CALL phase, a user may be provided with test questions and may be asked to answer them in the negative ("No"). If the user decides not to answer a test question or answers a test question in the positive ("Yes"), the question may be substituted by a question of the same type. For example, if a user is provided with a C question and the user decides not to answer the question, the C question may be replaced by another C question.

In a SPONG phase, a user may be asked test questions to verify personal data provided in the START phase of the pre-test. For example, a user may be asked "Is your birthday really on 10 Apr. 1992, as you stated earlier?". Physiological indices may be recorded during the provision of an answer to the question and may be compared to the average values of the physiological indices.

A deviation from the average values of the physiological indices of more than 25% may indicate that the given answer to the question is a lie. Thus, the SPONG phase allows the provision of test questions to a user to check on previously provided personal data.

Some embodiments may include monitoring physiological indices of a user during the steps of: providing the user with the plurality of test questions; and receiving answers from the user to the test questions (step 108). In an embodiment, a processor e.g. processor 204 of computing device 205 is configured to monitor physiological indices of a user during the steps of: providing the user with the plurality of test questions; and receiving answers from the user to the test questions. In an embodiment, by monitoring physiological indices during steps of providing the user with the plurality of test questions and receiving answers from the user to the test questions, the machine learning algorithm may dynamically evaluate the physiological indices and may reorder questions during the provision of test questions to the user. Thus, the test questions can be adjusted to the behavior of the user during the polygraph test in response to the physiological indices and may allow to generate questions that are likely to show a significant differentiation between a true answer and a false answer.

Some embodiments may include comparing baselines and the monitored physiological indices during the provision of answers to the test questions (step 110). In an embodiment, a processor e.g. processor 204 of computing device 205, is configured to compare baselines and monitored physiological indices during the provision of answers to the test questions. For example, in the MAP phase, a user may be provided with test questions generated by the machine learning algorithm. A user may be repeatedly asked to provide answers to a plurality of test questions. For example, a plurality of test questions may be asked 3-5 times. The physiological indices may be evaluated by comparison of the physiological indices detected for a user in a period of time when answering a test question with the average value of physiological indices measured in the pre-test.

In another embodiment, changes in physiological indices may be compared between C questions and R questions.

A baseline that is generated and set in the analyzing step of answers to the pre-questions and physiological indices may be adjustable based on the monitored physiological indices of a user and answers received from a user to the test questions. For example, a baseline for a physiological index, such as heart rate may be set after analysis of the answers to the pre-questions and the monitored heart rate of a user via machine learning. In an embodiment, a baseline may be set by calculating the average heart rate from the monitored heart rates during the pre-test. During the provision of test questions, a baseline, e.g. a baseline for the heart rate, may be adjusted using machine learning. Changes of the physiological indices during the pre-test questions may be analyzed using machine learning to identify the magnitude by which the physiological conditions of a user change when the user answers a question. The magnitude of changes in physiological conditions, for example heart rate, during previous questions such as pre-test questions may allow to identify an underlying change in the users physiological conditions when answering a question that occurs irrespective whether a user truthfully answers a question or when a user answers a test question by telling a lie. For example, when a user is provided with an R test question and a value of a physiological index, e.g. heart rate, increases by more than 20% during the time period in which the user answers the R test question, a baseline of the heart rate may be increased by 5%.

When a user is provided with a C test question or a SYM test question and a value of a physiological index, e.g. heart rate, increases by more than 20% during the time period in which the user answers the C test question, a baseline of the heart rate may be decreased by 5%. The adjustment of the baseline after answering a test question prior to the next test question of the polygraph test may allow to take into account changes to the physiological conditions that occur during the polygraph test. For example, the adjustment of a baseline may allow to compare physiological indices for a user when answering subsequent questions using a baseline that reflects previous changes to the user's physiological indices prior to answering the subsequent question.

In one embodiment, the step of comparing a baseline and the monitored physiological indices during the provision of answers to a test question may also include the adjustment to a period of time that is considered when a user answers a provided test question. For example, a change of physiological indices after the provision of a question to a user is monitored in a time window of seconds immediately starting after the provision of a question to the user. The time window may be adjusted in relation to the gender of a user. For example, the time window may be decreased by 1 second if the user is male or the time window may be increased by a second if the user is female. The time window may, for example, be increased by 1 second if the user is over 40 years old and the time window may be decreased by 1 second if the user is under 40 years old.

Some embodiments may include generating a test result to the test questions (step 112). In one embodiment, a processor e.g. processor 204 of computing device 205 is configured to generate a test result for the test questions. A test result to the test questions may be generated using machine learning from the monitored physiological indices measured during the steps of providing the user with the plurality of test questions and receiving answers from the user to the test questions. In one embodiment, a test result for a test question may be generated by analyzing the changes in physiological indices when a question is answered relative to the baseline. A test result may be generated by analyzing the changes in physiological indices when a question is answered relative to the baseline for one or more physiological indices. Using machine learning, the system may compare relative changes for physiological indices. Physiological indices that show a large deviation from the baseline can be considered to be more indicative for the assessment of whether a user answered a question truthfully or by answering the question with a lie compared to small changes in relative indices. Therefore, physiological indices for which large changes in physiological indices in response to a question have been monitored will be identified using machine learning and are considered more indicative to differentiate between truth and lie. Thus, in generating a test result to a test question using more than one physiological index, machine learning may weight physiological indices showing large changes in physiological indices in response to a question higher than physiological indices showing small changes in physiological indices in response to a question. For example, if a change of a respirator rate has been calculated as 10% in relation to the respirator rate baseline and a change of heart rate has been calculated as 30% in relation to the heart rate baseline, machine learning will weigh the change in the heart rate higher than the change in respiratory rate when generating a test result to the corresponding test question.

Test results to a plurality of test question may be generated after repeatedly asking the test questions. For example, a plurality of test questions may be asked in one or more question cycles, for example three cycles. In each of the question cycles, physiological indices may be monitored in a specific time period. Values for physiological indices are normalized as disclosed herein and the changes in the normalized physiological indices may be compared for a question for each of the question cycles in relation to a baseline for each of the physiological indices. For example, a change in physiological indices may be identified to be similar, e.g. having the same magnitude, for a test question in each of the question cycles. In an embodiment, the time period for each test cycle may be adjusted using machine learning, for example based on changes to physiological indices identified in a previous test cycle. For example, if a change in physiological index is found to occur between 7-12 seconds after answering a test question A by a user during a monitored time period of 30 seconds after answering the test question, the time period for monitoring physiological indices for that test question may be reduced from 30 seconds to 15 seconds. Thereby, the overall polygraph test may be shortened to achieve an overall polygraph test in a shorter period of time.

In one embodiment, changes to physiological indices may be compared between C questions and R questions. Changes in normalized physiological indices may be calculated for each of the physiological indices that are recorded during a polygraph test. In an embodiment, four physiological indices such as heart rate, blood pressure, blood saturation and respiratory rate of a user may be monitored during a polygraph test. Changes to physiological indices monitored during a polygraph test may be assessed during machine learning by comparing normalized values for physiological indices for a question between one or more question cycles but can also be compared between different physiological indices monitored during the provision of an answer by a user to the same test question: For example, if changes in normalized physiological indices for a C question are greater than 4 points in relation to a R question, a positive test result is obtained; if the changes in normalized physiological indices for a R question are greater than 4 points in relation to a C question, a negative test result is obtained. If the changes in normalized physiological indices for a C question are lower than 4 points in relation to a R question, an inconclusive test result is obtained; if the changes in normalized physiological indices for a R question are lower than 4 points in relation to a C question, an inconclusive test result is obtained.

In addition to the generation of a test result to a test question, the polygraph test may generate a purity index that is indicative of the validity of the polygraph test. Using machine learning, the behavior of the user during the polygraph test can be evaluated by reviewing the physiological indices monitored during the polygraph test. A purity index may be generated in the assessment of the quality of monitored physiological indices. During a polygraph test, using machine learning, missing data points in the monitoring of physiological indices may be identified and may be set in relation to the overall number of theoretically monitored physiological indices during a polygraph test. A purity index may thereby be generated for each of the measured physiological indices. For example, one or more physiological indices may be monitored in certain time intervals for example every second. If, for example, a sensor developed a fault and a heart rate could not be monitored for a period of time during the polygraph test, the number of monitored data points for a physiological index is lower than the theoretical number of data points for the period of time.

Accordingly, the ratio of obtained data points for a physiological index in relation to the theoretical obtainable number of data points for a physiological index multiplied by 100 may generate a score that reflects the purity of the recorded values of the physiological indices. In an embodiment, the purity index may also be an indicator for the quality of the user interaction during the polygraph test. For example, if a user interrupts a polygraph test intentionally or unintentionally, for example by holding the mobile device in a position that does not allow to monitor physiological indices, the purity index may reflect the lack of data points for a physiological index as a result.

Using machine learning, missing data points for physiological indices may be compensated for example, by interpolation of data points or adjusting the value for the missing data point of a physiological index to the previous or subsequent value.

A purity index may also be generated in the assessment of a test result allow to assess the quality of monitored physiological indices for the generation of a test result for a test question. For example, test questions of a polygraph test may be repeated in one or more cycles and changes in physiological indices for the same test question may be compared in each of the one or more cycles. Using machine learning, the purity level in the generation of a test result for a test question may be generated after each cycle and the number of cycles may be varied depending on the purity level that has been identified for a test result. For example, in case that a clear differentiation between truth and lie could be generated for all test questions in all cycles of a polygraph test, the purity index is 100.

Since the evaluation of the changes to the physiological indices are evaluated using machine learning, the analysis is not affected by any form of bias that a human examiner may be exposed to during the polygraph test.

Figure 4:
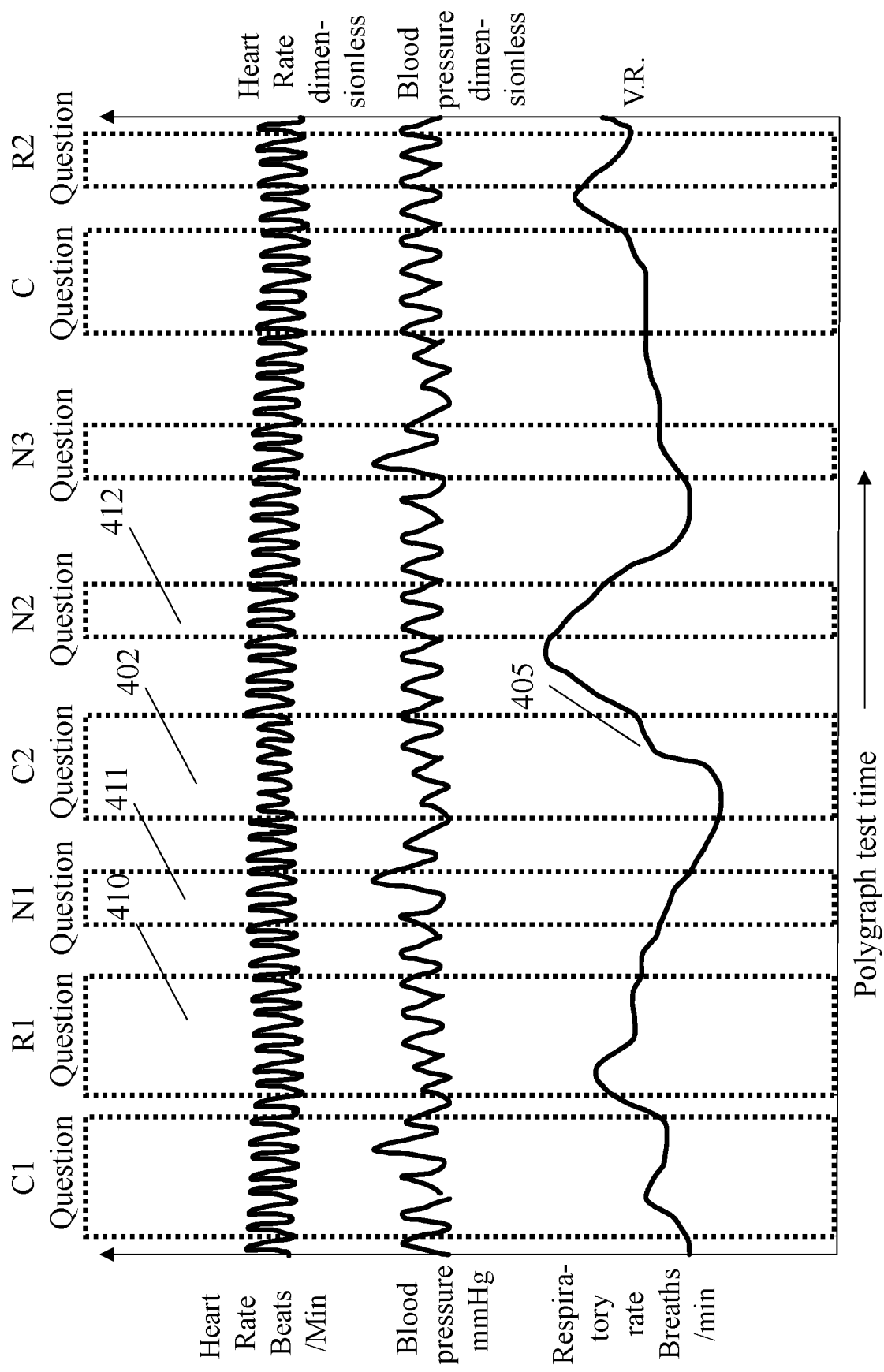
FIG. 4 is an exemplary graph of a polygraph, according to embodiments of the present invention.

FIG. 4 is an exemplary graph of a polygraph test method 100 as disclosed herein. Physiological indices such as heart rate, blood pressure and respiratory rate are shown in relation to the polygraph test time. Intervals for the monitoring of physiological indices during the provision of answers are indicated in relation to the type of questions C, R and N. During the time interval 402 for Question C2, a strong increase 405 in respiratory rate for a user can be observed. Blood pressure and heart rate remain fairly constant. In view of the decrease in respiratory rate during time periods 410, 411 and 412 for questions R1, N1 and N2, the increase in respiratory rate during the time period for Question C2, The answer provided by a user in response to question C2 may be assessed by the system as a deliberate lie.

Example CQT Polygraph Test

After conducting a pre-test that includes monitoring of physiological indices to set a baseline for the subsequent test questions of the CQT test, the CQT test, carried out by the system disclosed herein, may comprise three cycles of test questions. Each test cycle may include three C/R test questions—two C questions and one R question. Physiological indices for example: oxygen saturation of blood (SPO2), blood pressure (RR), heart rate (HR), standard deviation of the interbeat intervals of normal sinus beats (SDNN) and SL for a user undergoing a polygraph test are recorded.

Figure 5:
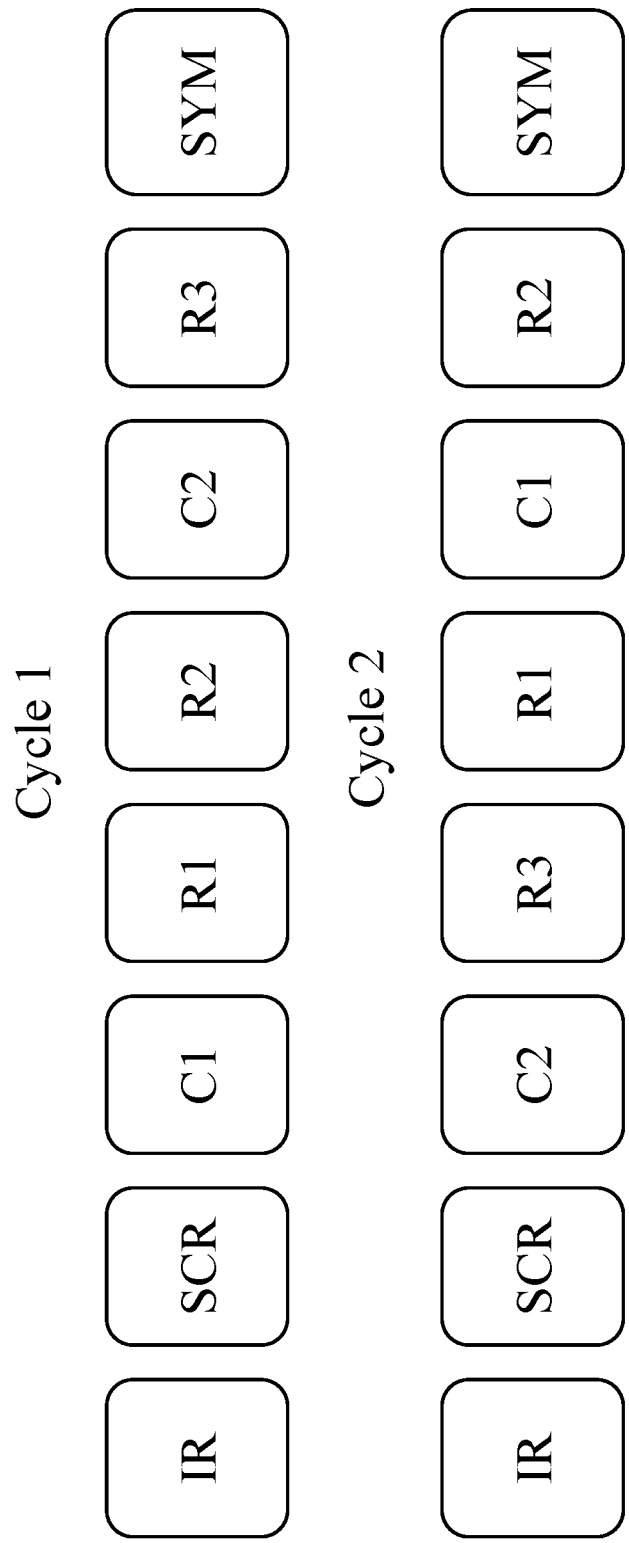
FIG. 5 shows exemplary cycles 1 and 2 of test questions forming part of the polygraph, according to embodiments of the present invention.

FIG. 5 is an exemplary order of test questions for cycle 1 and cycle 2 of a polygraph test, according to embodiments of the present invention. Test questions C1, C2, R1, R2 and R3 have been reordered in the second cycle of the polygraph test. The order of the test questions in the second test cycle may be identified using machine learning. Thereby, the order of the test questions may be generated by assessing the changes to the physiological indices of a user undergoing the polygraph test in the first test cycle. Reordering of the test questions may allow to consider the effect of a strong change in physiological indices in response to a test question that may influence the monitored physiological indices in subsequent test questions.

FIG. 6 is an exemplary chart showing generated test questions for a polygraph test, according to embodiments of the present invention. In the present chart, six questions are shown that have been generated after the analysis of the answers to the pre-test questions and physiological indices using machine learning. The questions are classed by its question type e.g. IR, SCR, C, R or SYM, the language of the question and whether dynamic values, e.g. name of the user, that are specific to the user undergoing the polygraph test. Dynamic values for test questions may have been recorded during the pre-test and are used in the generation of test question using machine learning. The chart disclosed in FIG. 6 may also disclose answers to the test question recorded for the user during the polygraph test ("yes" or "no").

In FIG. 7, an exemplary chart showing recorded physiological indices during a polygraph test for selected test questions is disclosed. For time intervals in which a user has been asked a test question and in which a user has provided an answer to a test question, physiological indices for the user may be recorded. Readings of physiological indices may be recorded every second. In the present example, physiological indices for HR, SPO2 and RR have been monitored every second for time intervals related to test questions C, R and during the break between questions C and R. In case of missing monitoring data, a data point for a certain physiological index, e.g. heart rate, may be interpolated based on a previous and a subsequently recorded data point for a physiological index.

The number of missing recordings of physiological indices and therefore the purity of the monitored physiological indices may be assessed by generating a purity index. For example, using machine learning, missing data points in the monitoring of physiological indices may be identified and may be set in relation to the overall number of theoretically monitored physiological indices during a polygraph test. A purity index may thereby be generated for each of the measured physiological indices.

Figure 8:
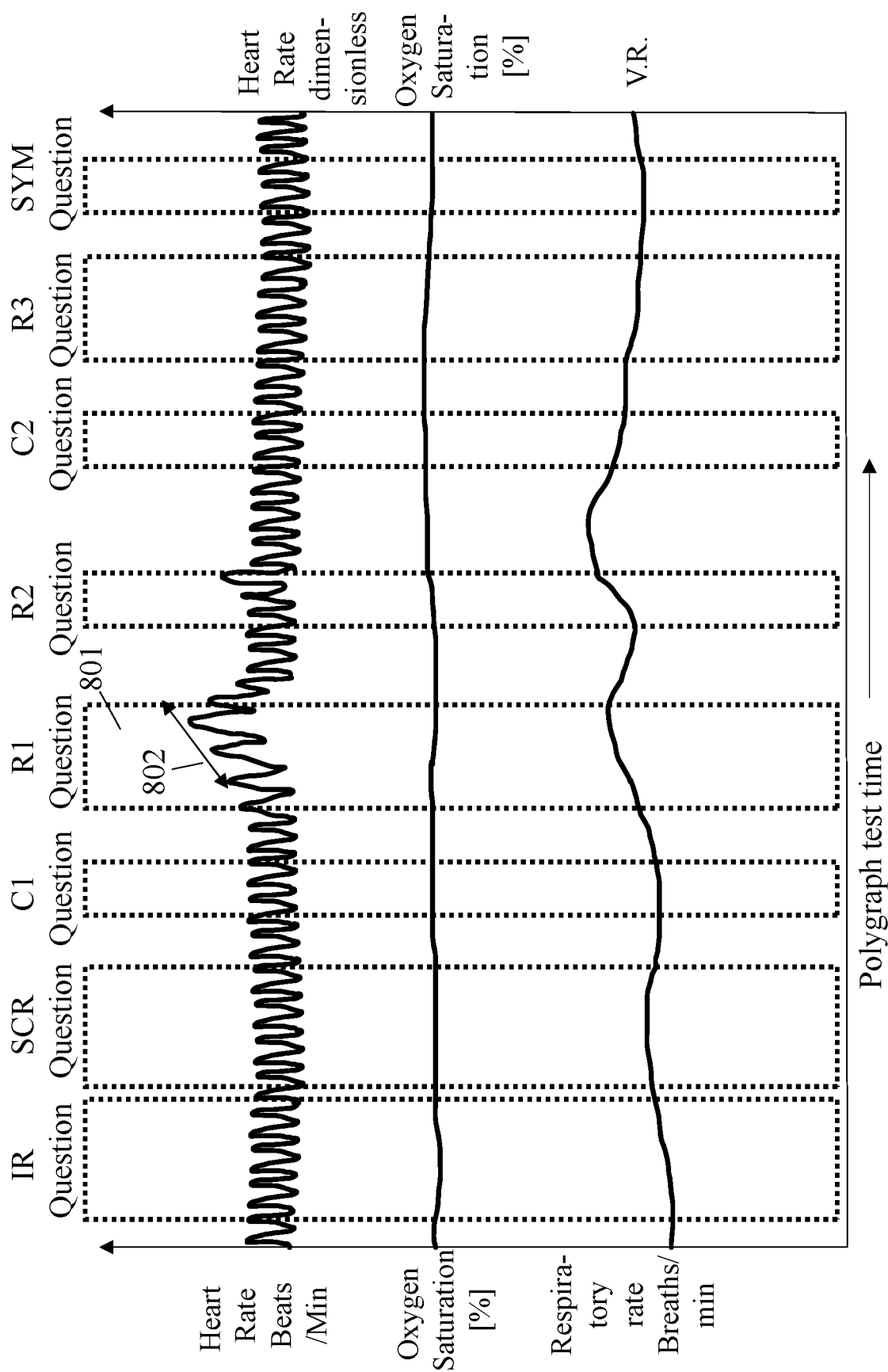
FIG. 8 is an exemplary graph of a polygraph, according to embodiments of the present invention.

FIG. 8 is an exemplary graph of a polygraph, according to embodiments of the present invention. The present example shows graphs for recorded, normalized physiological indices HR, SPO2 and RR that have been monitored every second during the polygraph test. For example, in the time interval for asking and answering test quest R1 801, the normalized heart rate significantly increased during the time interval related to question R1 802. The relative increase of the heart rate in relation to the baseline and the recorded time in which the increase in heart rate was monitored may be analyzed using machine learning, for example using a peak analysis algorithm to extract, for example, the highest increase in heart rate during the time interval corresponding to question R2.

Figure 9:
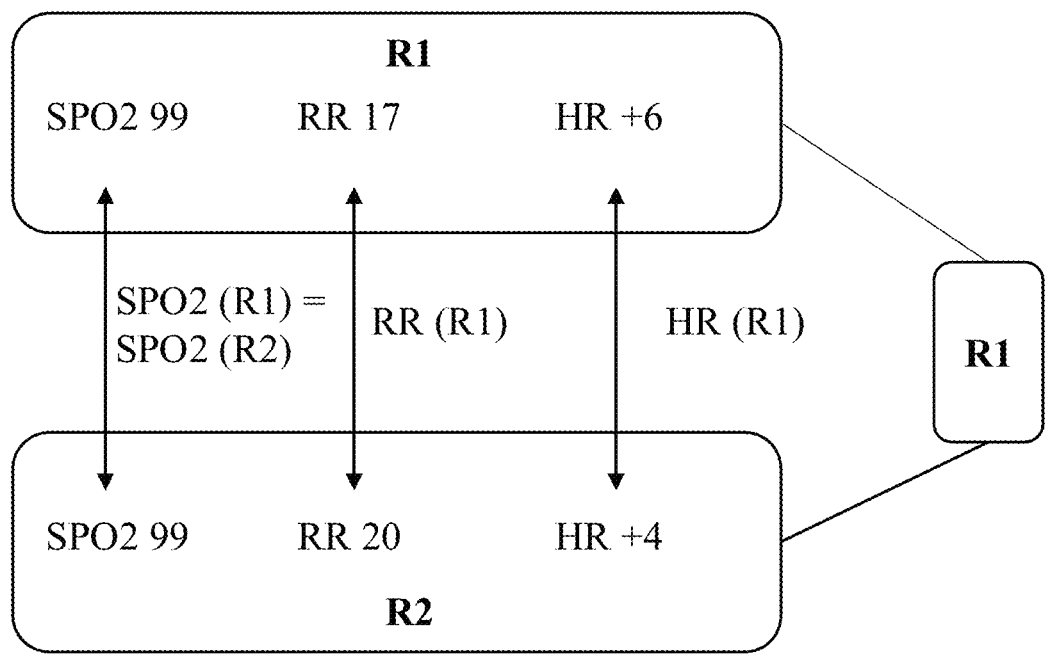
FIG. 9 is an exemplary visualization of the comparison of physiological indices for two R questions, according to embodiments of the present invention.

FIG. 9 is an exemplary visualization of a comparison of physiological indices for two R questions, according to embodiments of the present invention. In the present example, test question R1 led to monitored physiological indices of: SPO=99, RR=17 and HR+6. Test question R2 led to monitored physiological indices of: SPO=99, RR=20 and HR+4. Test question R1 showed a higher deviation of normalized physiological indices from the baseline for a user for physiological indices RR and HR compared to test question R2 and the same normalized physiological index for physiological index SPO2. Accordingly, test question R1 led to a stronger physiological response of a user than test question R2. Deviations of normalized physiological indices from recorded baselines for physiological indices may be compared for two test questions for given impact intervals. For example, an impact interval is the time interval starting 2 seconds after presenting a user with a test question until 12 seconds after the provision of an answer by a user. For physiological indices SPO2 and RR, an average value may be generated for a specific time interval, e.g. one second, and is then included in a chart showing recorded physiological indices for an impact interval. For physiological indices HR, SDNN and SL, the deviation from the baseline is analyzed using a peak analysis algorithm that allows the identification of the greatest deviation from a baseline for a specific time interval, e.g. an impact interval.

For each cycle of the polygraph test, the deviation of each of the monitored, normalized physiological indices from their corresponding baselines is compared for C questions within each test question cycle. Within each test question cycle, the C question showing the strongest deviation of its normalized physiological index from the baseline is then compared to the deviation from the baseline of the R questions (the normalized physiological index of the R question). In case an R question leads to a stronger deviation from its baseline than a C question, the score of a user undergoing a polygraph test is decreased by one point. In case that a C question leads to a stronger deviation from its baseline than an R question, the score of a user undergoing a polygraph test is increased by one point. A test result in relation to provided answers by a user undergoing the polygraph test is generated by evaluating the score that a user has obtained after conducting the test: if the score in relation to the physiological indices as a reaction to a C and R question is greater than 0, the user is answering the specific test question by telling the truth; if the score in relation to the physiological indices as a reaction to a C and R question is lower than 0, the user is answering the specific test question by telling a lie.

The aforementioned flowchart and diagrams illustrate the architecture, functionality, and operation of possible implementations of systems, methods and computer program products according to various embodiments of the present invention. In this regard, each portion in the flowchart or portion diagrams may represent a module, segment, or portion of code, which comprises one or more executable instructions for implementing the specified logical function (s). It should also be noted that, in some alternative implementations, the functions noted in the portion may occur out of the order noted in the figures. For example, two portions shown in succession may, in fact, be executed substantially concurrently, or the portions may sometimes be executed in the reverse order, depending upon the functionality involved, It will also be noted that each portion of the portion diagrams and/or flowchart illustration, and combinations of portions in the portion diagrams and/or flowchart illustration, can be implemented by special purpose hardware-based systems that perform the specified functions or acts, or combinations of special purpose hardware and computer instructions.

As will be appreciated by one skilled in the art, aspects of the present invention may be embodied as a system or an apparatus. Accordingly, aspects of the present invention may take the form of an entirely hardware embodiment or an embodiment combining software and hardware aspects that may all generally be referred to herein as a "circuit," "module" or "system."

The aforementioned figures illustrate the architecture, functionality, and operation of possible implementations of systems and apparatus according to various embodiments of the present invention. Where referred to in the above description, an embodiment is an example or implementation of the invention. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions. It will further be recognized that the aspects of the invention described hereinabove may be combined or otherwise coexist in embodiments of the invention.

It is to be understood that the phraseology and terminology employed herein is not to be construed as limiting and are for descriptive purpose only.

The principles and uses of the teachings of the present invention may be better understood with reference to the accompanying description, figures and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions.

For example, flow need not move through each illustrated box or state, or in exactly the same order as illustrated and described.

Methods of the present invention may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

The descriptions, examples and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention may be implemented in the testing or practice with materials equivalent or similar to those described herein.

While the invention has been described with respect to a limited number of embodiments, these should not be construed as limitations on the scope of the invention, but rather as exemplifications of some of the preferred embodiments. Other or equivalent variations, modifications, and applications are also within the scope of the invention. Accordingly, the scope of the invention should not be limited by what has thus far been described, but by the appended claims and their legal equivalents.

The invention claimed is:

1. A computer-implemented method for conducting a polygraph test, the method comprising:
    monitoring physiological indices of a user during the steps of:
        providing the user with a plurality of pre-questions; and
        receiving answers from the user to the plurality of pre-questions;
    analyzing the answers to the plurality of pre-questions and monitored physiological indices using machine learning and setting baselines for the monitored physiological indices;
    generating a plurality of test questions for the user based on the analysis;
    monitoring physiological indices of the user during the steps of:
        providing the user with the plurality of test questions; and
        receiving answers from the user to the plurality of test questions,
        wherein the plurality of test questions are dynamically modified during the provision of the test questions based on evaluation of received answers to the test questions using machine learning;
    comparing the baselines and the monitored physiological indices during the provision of the answers to the plurality of test questions; and
    generating a test result to the test questions, wherein said generation of said test result to said test questions comprises a quality assessment of said test result by calculating a ratio of non-detected data points for said monitored physiological indices to an overall number of theoretically monitored data points for said physiological indices monitored during said polygraph test.

2. A method according to claim 1, wherein the monitoring of physiological indices comprises measurement of cardio and respiratory factors.

3. A method according to claim 1, wherein the physiological indices are selected from a group consisting of: blood pressure, sweat, heart pulse, breathing, heart rate variation, respiratory rate, voice stress analysis and micro-reactions in facial muscles.

4. A method according to claim 1, wherein the baselines are continuously recalculated during the plurality of test questions based on dynamic monitoring of the physiological indices.

5. A method according to claim 1, wherein the baselines are adjusted to the answers of the user during the plurality of pre-questions and the plurality of test questions.

6. A method according to claim 1, wherein the plurality of pre-questions comprises questions on one or more of: personal data, credibility, personality traits and stimulation of the user.

7. A method according to claim 1, wherein the physiological indices are monitored using video processing of the user's face.

8. A method according to claim 1, wherein the monitored physiological indices are analyzed using machine learning to identify deviations in the physiological indices compared to the baselines for the monitored physiological indices.

9. A method according to claim 1, wherein the plurality of test questions are dynamically adjusted using machine learning based on the received answers to the plurality of pre-questions.

10. A method according to claim 9, wherein the dynamical adjustment of the plurality of test questions enables the generation of the plurality of test questions with an increased discernment in the monitored physiological indices upon answering the plurality of test questions.

11. A method according to claim 1, wherein the plurality of test questions is dynamically reordered based on the received answers to the plurality of pre-questions.

12. A method according to claim 1, wherein the plurality of test questions comprises a test question to identify the user.

13. A method according to claim 1, wherein the polygraph test is conducted remotely in absence of a human examiner.

14. A method according to claim 1, wherein the comparison of the baselines and the monitored physiological indices during the provision of answers to the plurality of test questions allows identification of the physiological indices with large percentage deviation relative to the baselines in the generation of test results for the plurality of test questions.

15. A system for conducting a polygraph test, the system comprising:
    a computing device;
    a memory; and
    a processor, the processor configured to:
        monitor physiological indices of a user during the steps of:
            providing the user with a plurality of pre-questions; and
            receiving answers from the user to the plurality of pre-questions;
        analyze the answers to the plurality of pre-questions and monitored physiological indices using machine learning and set baselines for the monitored physiological indices;
        generate a plurality of test questions for the user based on the analysis;
        monitor physiological indices of the user during the steps of:
            providing the user with the plurality of test questions; and
            receiving answers from the user to the plurality of test questions,
            wherein the plurality of test questions are dynamically modified during the provision of the test questions based on evaluation of received answers to the test questions using machine learning;
        compare the baselines and the monitored physiological indices during the provision of the answers to the plurality of test questions; and
        provide a test result to the test questions, wherein said test result to said test questions comprises a quality assessment of said test result by calculating a ratio of non-detected data points for said monitored physiological indices to an overall number of theoretically monitored data points for said physiological indices monitored during said polygraph test.

16. A system according to claim 15, wherein the monitoring of physiological indices comprises measurement of cardio and respiratory factors.

17. A system according to claim 15, wherein the physiological indices are selected from a group consisting of: blood pressure, sweat, heart pulse, breathing, heart rate variation, RR+, voice stress analysis and micro-reactions in facial muscles.

18. A system according to claim 15, wherein the baselines are continuously recalculated during the plurality of test questions based on dynamic monitoring of the physiological indices.

19. A system according to claim 15, wherein the baselines are adjusted to the answers of the user during the plurality of pre-questions and the plurality of test questions.

20. A computer-implemented method for carrying out a polygraph test, the method comprising:
    measuring physiological parameters of a user during the steps of:
        sending to the user a first series of test questions; and
        collecting answers from the user to the first series of questions;
    analyzing the answers to the first series of test questions and measured physiological parameters using machine learning;
    calculating baselines for the measured physiological parameters;
    generating a second series of test questions for the user based on the analysis;
    measuring physiological parameters of the user during the steps of:
        sending to the user the second series of test questions; and
        collecting answers from the user to the second series of test questions,
        wherein the plurality of test questions are dynamically modified during the provision of the test questions based on evaluation of received answers to the test questions using machine learning;
    comparing the baselines and the measured physiological parameters during the collection of the answers to the second series of test questions; and
    providing a test result to the second series of test questions, wherein said test result to said second series of test questions comprises a quality assessment of said test result by calculating a ratio of non-detected data points for said monitored physiological parameters to an overall number of theoretically monitored data points for said physiological parameters monitored during said polygraph test.

* * * * *